United States Patent [19]

Jacobsen et al.

[11] Patent Number: 5,109,001
[45] Date of Patent: Apr. 28, 1992

[54] FUSED 2,3-DIHYDROXYDIAZOLO COMPOUNDS AND THEIR PREPARATION AND USE

[75] Inventors: Poul Jacobsen, Rodovre; Flemming E. Nielsen, Virum; Tage Honoré, Copenhagen; Jorgen Drejer, Vaerlose, all of Denmark

[73] Assignee: Novo Nordisk A/S, Målov, Denmark

[21] Appl. No.: 570,819

[22] Filed: Aug. 22, 1990

Related U.S. Application Data

[62] Division of Ser. No. 369,762, Jun. 22, 1989, Pat. No. 4,977,155.

[30] Foreign Application Priority Data

Jun. 28, 1988 [DK] Denmark .................... 3567/88

[51] Int. Cl.⁵ ............. A61K 31/495; C07D 487/04; C07D 517/04; C07D 293/06
[52] U.S. Cl. ........................... 514/250; 544/345
[58] Field of Search ................ 514/250, 345

[56] References Cited

U.S. PATENT DOCUMENTS 4,912,108 3/1990 Jacobsen .................. 544/345

Primary Examiner—Mark L. Berch
Attorney, Agent, or Firm—Gordon W. Hueschen

[57] ABSTRACT

Heterocyclic dihydroxyquinoxaline compounds having the formula

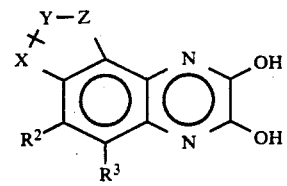

wherein
$R^2$ is hydrogen, $NO_2$, $NH_2$, CN, halogen, or $SO_2NH_2$;
—X—Y—Z— is selected from =N—Se—N=, =N—O—N=, =N—S—N=;
wherein $R^3$ is hydrogen, lower alkyl, or $CF_3$.

The invention also relates to a method of preparing the compounds, pharmaceutical compositions thereof, and their use.

The compounds are useful in the treatment of indications caused by hyperactivity of the excitatory neurotransmitters.

11 Claims, No Drawings

FUSED 2,3-DIHYDROXYDIAZOLO COMPOUNDS AND THEIR PREPARATION AND USE

This is a division of U.S. application Ser. No. 369,762, filed Jun. 22, 1989, now U.S. Pat. No. 4,977,155.

The present invention relates to therapeutically active heterocyclic compounds, a method of preparing the same, pharmaceutical compositions comprising the compounds, and a method of treating therewith.

The heterocyclic compounds of the invention have the general formula I

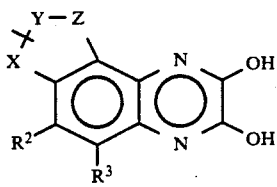

wherein
$R^2$ is hydrogen, $NO_2$, $NH_2$, CN, halogen, or $SO_2NH_2$;
—X—Y—Z— is selected from
—N=N—NR$^3$—, —NR$^3$—N=N—, =N—NR$^3$—N=, —S—CH=N—, —N=CH—S—, —CH=C(CO$_2$R$^3$)—S—, —S—C(CO$_2$R$^3$)=CH—, =N—Se—N=, —N=CR$^3$—NR$^3$—, —NR$^3$—CR$^3$=N—, =N—O—N=, —N=CR$^3$—CR$^3$=N—, —NH—CR$^3$=CR$^3$—CR$^3$=N—, —N=CR$^3$—CR$^3$=CR$^3$—NH, =N—S—N=;

wherein $R^3$ is hydrogen, lower alkyl, or $CF_3$.

When the group —X—Y—Z— is tetravalent, that is, has the formula =N—Se—N=, =N—O—N=, or =N—S—N=, or also =N—NR$^3$—N=, it is clear that the "A" ring cannot be aromatic, but must be dieneic, in which case the compound (I) has the formula:

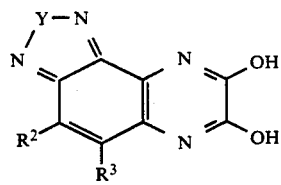

as further exemplified in this application by Examples 10, 11, 20, 23b, 24, 25c, 27, 37b, and 38, some of the compounds of which are respectively claimed in the species claims hereof.

The compounds of the invention can be prepard by methods well known in the art and for example by:

a) reacting a compound having the formula II

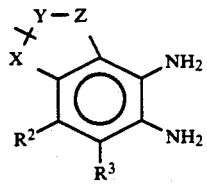

wherein —X—Y—Z—, $R^2$ and $R^3$ have the meanings set forth above, with oxalate or a reactive derivative thereof to form a compound of formula I, or b) refluxing a compound having the formula III

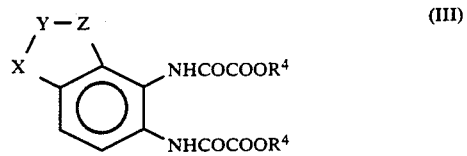

wherein —X—Y—Z—, $R^2$ and $R^3$ have the meanings defined above, and wherein $R^4$ is lower alkyl, in a mineral acid, to form a compound of formula I.

L-glutamic acid, L-aspartic acid and a number of other closely related amino acids have in common the ability to activate neurons in the central nervous system (CNS). Biochemical, electrophysiological and pharmacological studies have substantiated this and demonstrated that acidic amino acids are transmitters for the vast majority of excitatory neurons in the mammalian CNS.

Interaction with glutamic acid mediated neurotransmission is considered a useful approach in the treatment of neurological and psychiatric diseases. Thus, known antagonists of excitatory amino acids have shown potent antiepileptic and muscle relaxant properties (A. Jones et al., Neurosci. Lett. 45, 157–61 (1984) and L. Turski et al., Neurosci. Lett. 53, 321–6 (1985)).

It has been suggested that accumulation of extracellular excitatory and neurotoxic amino acids, followed by hyperstimulation of neurons, may explain the neuronal degenerations seen in neurological diseases as Huntingtons chorea, Parkinsonism, epilepsia, senile dementia, and deficiencies of mental and motoric performance seen after conditions of brain ischemia, anoxia and hypoglycemia (E. G. McGeer et al., Nature, 263, 517–19 (1976) and R. Simon et al., Science, 226, 850–2 (1984).

Excitatory amino acids exert their actions via specific receptors located postsynaptically or presynaptically. Such receptors are at present conveniently subdivided into three groups based on electrophysiological and neurochemical evidence: 1 the NMDA (N-methyl-D-aspartate) receptors, 2 the quisqualate receptors, and 3 the kainate receptors. L-glutamic acid and L-aspartic acid probably activate all the above types of excitatory amino acid receptors and possibly other types as well.

The consequence of excitatory amino acid interaction with postsynaptic receptors is an increase in intracellular cGMP levels (G. A. Foster et al., Life Sci. 27, 215–21 (1980)) and an opening of $Na^+$-channels (A. Luini et al., Proc. Natl. Acad. Sci. 78. 3250–54 (1981)). $Na^+$-influx in the neurons will depolarize the neuronal membranes, initiate an action potential and ultimately lead to a release of transmitter substance from the nerve terminal. The effects of test compounds on the above mentioned secondary responses to receptor interaction can be tested in simple in vitro systems.

The above mentioned classification of excitatory amino acid receptors into NMDA, quisqualate, and kainate receptors is based primarily on the following electrophysiological and neurochemical findings.

1) N-methyl-D-aspartate (NMDA) receptors exhibit high selectivity for the excitant NMDA. Ibotenic acid, L-homocysteic acid, D-glutamic acid and trans-2,3-piperidine dicarboxylic acid (trans-2,3-PDA) exert a strong to moderate agonist activity on these receptors. The most potent and selective antagonists are the D-isomers of the 2-amino-5-phosphonocarboxylic acids, e.g., 2-amino-5-phosphono-valeric acid (D-APV) and 2-amino-7-phosphonoheptanoic acid (D-APH), while moderate antagonist activity is shown by the D-isomers of long chain 2-amino dicarboxylic acids (e.g.,D-2-amino-adipic acid) and long chain diaminodicarboxylic acids (e.g.,diaminopimelic acid). The NMDA-induced synaptical responses have been extensively investigated in the mammalian CNS, especially in the spinal cord (J. Davies et al., J. Physiol. 297, 621–35 (1979) and the responses have been shown to be strongly inhibited by $Mg^{2+}$.

It is well known that NMDA antagonists have anticonvulsant activity against seizures of diverse origin (Jones et al., Neurosci. Lett. 45, 157–61 (1984)), and that the potencies of the substances in seizure tests correlate well with the ability of the compounds to block NMDA responces in in vivo and in vitro electrophysiological experiments (Watkins et al., Annu. Rev. Pharmacol. Toxicol. 21, 165–204 (1981)).

NMDA antagonists are therefore useful as anticonvulsants, especially as anti-epileptics.

2) Quisqualate receptors are activated selectively by quisqualic acid, other potent agonists being AMPA (2-amino-3-hydroxy-5-methyl-4-isoxazolepropionic acid) and L-glutamic acid. Glutamic acid diethyl ester (GDEE) is a selective but very weak antagonist of this site. Quisqualate receptors are relatively insensitive to $Mg^{2+}$.

It is well known that an excitatory aminoacid projection from prefrontal cortex to nucleus accumbens (a special part of the forebrain having dopamine neurons) exists (Christie et al., J. Neurochem. 45, 477–82 (1985)). Further it is well known that glutamate modulates the dopaminergic transmission in the striatum (Rudolph et al., Neurochem. int. 5, 479–86 (1983)) as well as the hyperactivity connected with presynaptic stimulation of the dopamine system with AMPA in nucleus accumbens (Arnt. Life Sci. 28, 1597–1603 (1981)).

Quisqualate antagonists are therefore useful as a new type of neuroleptic.

3) Kainate receptors. Excitatory responses to kainic acid are relatively insensitive to antagonism by NMDA-antagonists and by GDEE, and it has been proposed that kainic acid activates a third subclass of acidic amino acid receptor. Certain lactonized derivatives of kainic acid are selective antagonists (O. Goldberg et al., Neurosci. Lett. 23, 187–91 (1981)) and the dipeptide 3-glutamyl-glycine also shows some selectivity for kainate receptors. $Ca^{2+}$ but not $Mg^{2+}$ is a strong inhibitor of kainic acid binding.

The affinity of a substance for one or more of the different types of excitatory amino acid receptors may be studied in simple binding experiments. In essense, the method involves incubation of a particular selected radiolabelled ligand and the particular specific substance to be investigated with brain homogenate which contains the receptor. Measurement of receptor occupancy is made by determination of the radioactivity bound to the homogenate and subtraction of nonspecific binding.

The influence of glutamic acid analogues on secondary effects of glutamate receptor interactions, such as on c-GMP formation and on $Na^+$-efflux, may be studied in vitro by using brain slices. Such experiments will provide information as to the efficacies (agonist/antagonist) of the test substances. This is in contrast to binding studies, which only provide information on the affinities of the compounds for the receptor.

It has now been found that the heterocyclic compounds of the invention have affinity for the glutamate receptors and are antagonists in connection with these types of receptors, which makes them useful in the treatment of any of the numerous indications caused by hyperactivity of excitatory amino acids.

The quisqualate receptor binding activity of the compounds of the present invention can be illustrated by determining their capability for displacing radioactively labelled 2-amino-3-hydroxy-5-methyl-4-isoxazolepropionic acid (AMPA) from the quisqualate type receptors.

The quisqualate antagonistic properties of the compounds is demonstrated by their capability to antagonize quisqualic acid stimulated $Na^+$-efflux from rat striatal slices.

The NMDA antagonistic properties of the compounds is illustrated by determining their capability to antagonize NMDA stimulated $^3H$-GABA release from cultured mouse cortex neurons.

The displacement activity of the compounds may be shown by determining the $IC_{50}$ value which represents the concentration (µg/ml) which causes a displacement of 50% of the specific binding of $^3H$-AMPA.

The quisqualate antagonism is measured by determining the $EC_{50}$ value which represents the concentration which reduces the rate of quisqualic acid stimulated sodium efflux by 50%.

The NMDA antagonistic activity of the compounds may be shown by determining the IC50 value, which represents the concentration (µg/ml) which inhibits 50% of NMDA induced $^3H$-GABA release.

$^3H$-AMPA binding (Test 1)

500 µl of thawed rat cerebral cortical membrane homogenate in Tris-HCl (30 mM), $CaCl_2$ (2.5 mM) and KSCN (100 mM) pH 7.1 were incubated at 0° C. for 30 min. with 25 µl H-AMPA (5 nM final concentration) and the test compound and buffer. Nonspecific binding was determined by incubation with L-glutamic acid (600 µM final concentration). The binding reaction was terminated by adding 5 ml of ice-cold buffer followed by filtration through Whatman GF/C glass fibre filters and 2×5 ml wash with ice-cold buffer. Bound radioactivity was measured by scintillation counting. $IC_{50}$ was determined by Hill analysis of at least four concentrations of test compound.

Antagonism of quisqualic acid induced $^{22}Na^+$-release (Test 2)

Slices from rat striatum were preincubated with $^{22}Na^+$ for 30 min. After the $^{22}Na^+$ loading period, the slices were successively and every minute transferred through a series of tubes, each containing 1.5 ml of a non-radioactive physiological solution saturated with $O_2$, with the help of a basket shaped sieve. Quisqualic acid (2 pg/ml) was present in the last 5 tubes and the compound to be tested was present in the same 5 tubes plus 3 tubes before. The amount of radioactivity in each washout tube as well as that left in the slices at the end of the experiment was measured by scintillation counting. $EC_{50}$-values were calculated by Hill analysis from at least three different concentrations of test compound as the concentration of test compound which reduces the efflux rate of $^{22}Na^+$-ions to 50% of the efflux rate in the absence of test compound.

Inhibition of NMDA stimulated $^3$H-GABA release from cultured mouse cerebral cortex interneurons (Test 3)

Release experiments are performed using the model described by Drejer et al. (Life Sci. 38, 2077 (1986)). To cerebral cortex interneurons cultured in petri dishes (30 mm) are added 100 µg/ml 3-vinyl-GABA one hour before the experiment in order to inhibit degradation of GABA in the neurons. 30 min before the experiment 5 µCi $^3$H-GABA is added to each culture and after this preloading period the cells are washed twice with a HEPES (N-2 Hydroxyethylpiperazine-N'-2-ethanesulfonic acid) buffered saline (HBS) containing 10 mM HEPES, 135 mM Nacl, 5 mM KCl, 0.6 mM MgSO$_4$, 1.0 mM Cacl$_2$ and 6 mM D-glucose; pH 7 and placed in a superfusion system. This system consists of a peristaltic pump continuously delivering thermostated 37° C. superfusion medium from a reservoir to the top of a slightly-tilted petri dish. The cell monolayer at the bottom of the dish is covered with a piece of nylon mesh to facilitate dispersion of medium over the cell layer. The medium is continuously collected from the lower part of the dish and delivered to a fraction collector. Initially, the cells are superfused with HBS for 15 min (flow rate 2 ml/min). Then cells are stimulated for 30 sec every 4 min by changing the superfusion medium from HBS to a corresponding medium containing NMDA and antagonists according to the following scheme:

| stimulation no. 1: | 3 µg/ml NMDA |
| stimulation no. 2: | 3 µg/ml NMDA + 0.3 µg/ml antagonist |
| stimulation no. 3: | 3 µg/ml NMDA + 3 µg/ml antagonist |

Test substances are dissolved in water or 48% ethanol. The final ethanol concentration in the assay must not exceed 0.1%.

The release of $^3$H-GABA in the presence of NMDA (stimulated relase in cpm) are corrected for the mean basal release (cpm) before and after the stimulation.

The stimulated release in the presence of antagonists are expressed relative to the stimulated release by NMDA alone and the IC$_{50}$ value for the antagonist is calculated (the concentration (µg/ml) of the test substance which inhibits 50% of the NMDA induced $^3$H-GABA release) either from a dose response curve or from the formula:

$$ID_{50} = \text{(applied test substance concentration)} \times \frac{1}{\left[\frac{C_o}{C_x} - 1\right]} \ \mu g/kg$$

where $C_o$ is stimulated release in control assays and $C_x$ is the stimulated release in the test assay (the calculation assumes normal mass-action interaction). 25–75% inhibition of the NMDA stimulation must be obtained, before calculation of IC$_{50}$.

Test results obtained by testing some compounds employed in the present invention will appear from the folowing table 1.

TABLE 1

| Compound of Example | Test 1 IC$_{50}$ µg/ml | Test 2 EC50 µg/ml | Test 3 IC$_{50}$ µg/ml |
| --- | --- | --- | --- |
| Ex 1:  | 13,3 |     |       |
| Ex 2:  | 0,85 | 10  | 0,26  |
| Ex 4:  | 10   |     |       |
| Ex 6:  | 0,31 | 4,1 | 0,096 |
| Ex 9:  | 0,41 |     | 0,14  |
| Ex 11: | 0,36 |     | 0,14  |
| Ex 13: | 0,07 |     | 0,11  |
| Ex 15: | 0,19 |     | 0,73  |
| Ex 17: | 0,21 |     |       |
| Ex 24: | 0,23 |     | 0,13  |
| Ex 35: | 0,39 |     | 0,1   |
| Ex 36: | 0,39 |     | 0,14  |
| Ex 38: | 0,13 |     | 0,09  |
| Ex 39: | 1,9  |     |       |

The invention will now be described in further detail with reference to the following examples.

EXAMPLE 1

7,8 Dihydroxy-1H-1,2,3-triazolo[4,5-f]quinoxaline

A suspension of 4-amino-5-nitrobenzotriazole (0.72 g, 4 mmol) in 100 ml of ethanol and 1 ml of conc. hydrochloric acid was hydrogenated at atmospheric pressure and room temperature for 6 h in the presence of 100 mg of 5% palladium-on-charcoal. The mixture was filtered and the catalyst was washed with about 50 ml of water. The combined filtrate was evaporated to dryness giving 0.70 g of the 4,5-diamino-benzotriazole as an hydrochloride. A solution of the crude diamino compound in 40 ml of 4M hydrochloric acid was refluxed with oxalic acid dihydrate (0.50 g, 4 mmol) for 3 h. The mixture was cooled on ice, and pH was adjusted to 5–6 with 2N sodium hydroxide. The precipitate was filtered off and washed with water and ethanol. It was then dissolved in 10 ml of 2N sodium hydroxide, treated with decolourising charcoal, and filtered. After adjustment to pH 6–7 with 4M hydrochloric acid the reprecipitated product was isolated, washed with water and ethanol, and dried at 100° C. affording 0.12 g (15%) of pure title compound; m.p. >300° C.; IR (KBr): 3200–2000, 1670 cm$^{-1}$; $^1$H-NMR (DMSO-d$_6$): 6.9 (broad s, 3H, NH+2OH); 7.03 (d,J=8 Hz, 1H, ArH); 7.43 (d,J=8 Hz,1H, ArH).

EXAMPLE 2

7,8-Dihydroxy-4-nitro-1H-1,2,3-triazolo[4,5-f]quinoxaline

Finely powdered potassium nitrate (3.1 g, 30.7 mmol) was added to a stirred solution of 7,8-dihydroxy-1H-1,2,3-triazolo[4,5-f]quinoxaline (6.1 g, 30 mmol) in 50 ml of conc. sulfuric acid at 0° C. (ice bath). The mixture was stirred over night at room temperature. Then a further amount of potassium nitrate (3 g) was added with cooling on an ice bath, and stirring was continued for 5 h at room temperature. The mixture was poured into 700 ml of ice/water, and the yellow precipitate was isolated, washed with water, and recrystallized from ethanol giving 5.2 g (70%) of the title compound; m.p. >300° C.; IR (KBr): 3300–2200, 1700 cm$^{-1}$;

$^1$H-NMR (DMSO-d$_6$): 8.13 (s, 1H, ArH), 11–16 (broad, 3H, NH +2OH).

EXAMPLE 3

4-Amino-7,8-dihydroxy-1H-1,2,3-triazolo[4,5-f]quinoxaline

A solution of stannous chloride dihydrate (6.0 g, 26.6 mmol) in 27 ml of conc. hydrochloric acid was added dropwise to a stirred suspension of 7,8-dihydroxy-4-nitro-1H-1,2,3-triazolo[4,5-f]quinoxaline (2.0 g, 8.1 mmol) in 13 ml of conc. hydrochloric acid. The mixture was stirred at 60° C. for 2 h, and then cooled on an ice bath. The precipitate was isolated by filtration and washed with cold conc. hydrochloric acid. The crude product was dissolved in 40 ml of hot 2N sodium hydroxide, filtered while hot, and adjusted to pH 5-6 with 4M hydrochloric acid. The precipitated solid was filtered, washed with water and dried to yield 1.63 g (93%) of the amino compound, m.p. >300° C., IR (KBr): 3450, 3350, 3230-2200, 1700-1600 cm$^{-1}$; $^1$H-NMR (DMSO-d$_6$): 5.8 (broad s, 2H, NH$_2$), 6.28 (s, 1H, ArH).

EXAMPLE 4

4-Cyano-7,8-dihydroxy-1H-1,2,3-triazolo[4,5-f]quinoxaline

4-Amino-7,8-dihydroxy-1H-1,2,3-triazolo[4,5-f]quinoxaline (0.44 g, 2 mmol) was suspended in 20 ml of 2M sulfuric acid and diazotised at 0° C. with sodium nitrite (0.18 g, 2.6 mmol) in 4 ml of water. After stirring at 0° C. for 30 min the diazosuspension was adjusted to pH 7 with solid sodium hydrogen carbonate, and a solution of potassium tetracyanonickelate (1.3 g) in 20 ml of water was added in one portion. Stirring was continued for 1 h at 0° C. and then the mixture was heated on a steam-bath for 30 min. After cooling on ice, the mixture was adjusted to pH 5 and filtered. The isolated dark solid was washed with water and recrystallized from ethanol with decolourising charcoal affording 20 mg (4.3%) of pure title compound, m.p. >300° C.; IR (KBr): 3300-2300, 2240, 1690 cm$^{-1}$.

EXAMPLE 5

7,8-Dihydroxy-1-methyl-1H-1,2,3-triazolo[4,5-f]quinoxaline

A solution of 6,7-diamino-1-methylbenzotriazole (1.63 g, 10 mmol) and oxalic acid dihydrate (2.0 g, 16 mmol) in 50 ml of 4M hydrochloric acid was refluxed on an oil bath for 2 h. The mixture was cooled on ice and the precipitate was collected by filtration, washed with water and ethanol affording 1.94 g (89%) of the title compound; m.p. >300° C.; IR (KBr): 3520-2400, 1700 cm$^{-1}$; $^1$H-NMR (DMSO-d$_6$): 4.63 (s, 3H, CH$_3$), 6.70 (d, J=9 Hz, 1H; ArH), 7.60 (d, J=9 Hz, 1H, ArH), 11.3 (very broad s, 1H, OH), 12.1 (broad s, 1H, OH).

EXAMPLE 6

7,8-Dihydroxy-1-methyl-4-nitro-1H-1,2,3-triazolo[4,5-f]quinoxaline

Finely powdered potassium nitrate (0.71 g, 7 mmol) was added portionwise to a stirred solution of 7,8-dihydroxy-1-methyl-1H-1,2,3-triazolo[4,5-f]quinoxaline (1.52 g, 7 mmol) in 28 ml of conc. sulfuric acid at 0° C. After about 1 h the ice bath was removed and stirring was continued over night at room temperature. Then an additional amount of potassium nitrate (0.7 g) was added and the mixture was stirred for 4 h at room temperature. Now the solution was poured into 150 ml of ice/water and the precipitated yellow solid was isolated by filtration and washed with water. Recrystallization from water/ethanol (1:1) afforded 1.2 g (65%) of the pure nitro compound; m.p. >300° C.; IR (KBr): 3600-2500, 1720 cm$^{-1}$; $^1$H-NMR (DMSO-d$_6$): 4.62 (s,3H, CH$_3$), 8.07 (s, 1H, ArH), 12.4 (broad s, 1H, OH, only one exchangeable proton could be seen).

EXAMPLE 7

4-Amino-7,8-dihydroxy-1-methyl-1H-1,2,3-triazolo[4,5-f]quinoxaline

A solution of stannous chloride dihydrate (2.26 g, 10 mmol) in 10 ml of conc. hydrochloric acid was added dropwise to a suspension of 7,8-dihydroxy-1-methyl-4-nitro-1H-1,2,3-triazolo[4,5-f]quinoxaline (0.79 g, 3 mmol) in 5 ml of conc. hydrochloric acid with stirring on an oil bath at 60°-70° C. Stirring was continued at this temperature for 90 min. Then the mixture was cooled on an ice bath, and filtered. The precipitate was washed with 1 ml of conc. hydrochloric acid. suspended in 150 ml of hot water and adjusted to pH 6-7 with solid sodium hydrogen carbonate. After reflux for 1 h the mixture was cooled on ice and the crude product was isolated by filtration, dissolved in 40 ml of hot 2N sodium hydroxide and reprecipitated with 4M acetic acid giving 0.16 g (23%) of the pure amino compound; m.p. >300° C.; IR (KBr): 3435, 3350, 3240, 3100-2400, 1690, 1640 cm$^{-1}$.

EXAMPLE 8

7,8-Dihydroxy-1H-pyrazolo[3,4-f]quinoxaline

A solution of 6,7-diaminoindazole hydrochloride (1.0 g, 5.4 mmol) in 10 ml of 4M hydrochloric acid was refluxed on an oil bath for 1½ h. The cooled mixture was filtered, and the isolated product was washed with water and ethanol, and dried in vacuo over phosphorus pentoxide affording 1.0 g (91%) of the pure title compound; m.p. >300° C.; IR (KBr): 3300-2000, 1700 cm$^{-1}$; $^1$H-NMR (DMSO-d$_6$): 6.3 (very broad s, 2H, NH and OH), 6.93 (d, J=9 Hz, 1H, ArH), 7.43 (d, J=9 Hz, 1H, ArH), 8.00 (s, 1H, H-3), 12.1 (broad s, 1H, OH).

EXAMPLE 9

7,8-Dihydroxy-4-nitro-1H-pyrazolo[3,4-f]quinoxaline

Finely powdered potassium nitrate (0.11 g, 1 mmol) was added to a stirred solution of 7,8-dihydroxy-1H-pyrazolo[3,4-f]quinoxaline (0.2 g, 1 mmol) in 2 ml of conc. sulfuric acid at room temperature. The solution was stirred for 1 h at this temperature and then poured into 50 ml of ice/water. After 30 min the precipitated solid was isolated by filtration and washed with water. Recrystallization from N,N-dimethylformamide/water afforded 0.13 g (53%) of the nitro compound; m.p. >300° C.; IR (KBr): 3300-2500, 1705 cm$^{-1}$; $^1$H-NMR (DMSO-d$_6$): 7.83 (s, 1H, ArH), 8.37 (s, 1H, ArH), 12.2 (broad s, 2H, 2OH).

EXAMPLE 10

7,8-Dihydroxy-2-methyl-2H-1,2,3-triazolo[4,5-f]quinoxaline

A solution of 4,5-diamino-2-methylbenzotriazole (2.5 g, 15.3 mmol) and oxalic acid dihydrate (2.5 g, 19.8 mmol) in 80 ml of 4M hydrochloric acid was refluxed on an oil bath for 1 h. The cooled mixture was filtered, and the precipitate was washed with water and ethanol. Recrystallization from ethanol with decolourising charcoal afforded 1.0 g (30%) of the title compound; m.p. >300° C.; IR (KBr): 3500– 2200, 1690 cm$^{-1}$; $^1$H-NMR (DMSO-d$_6$): 4.48 (s, 3H, CH$_3$), 7.25 (d, J=9 Hz, 1H, ArH), 7.60 (d, J=9 Hz, 1H, ArH), 12.03 (broad s, 1H, OH), 12.47 (broad s, 1H, OH).

EXAMPLE 11

7,8-Dihydroxy-2-methyl-4-nitro-2H-1,2,3-triazolo[4,5-f]quinoxaline

Finely powdered potassium nitrate (0.47 g, 4.6 mmol) was added to an ice-cooled solution of 7,8-dihydroxy-2-methyl-2H-1,2,3-triazolo[4,5-f]quinoxaline (1.0 g, 4.6 mmol). The mixture was stirred at 0° C. for 1½ h, then at room temperature for 4 h and finally poured into ice-/water. The resulting solution was extracted with ethyl acetate. The extract was dried over anhydrous sodium sulfate and concentrated to dryness giving 0.27 g (22%) of the nitro compound; m.p. >300° C.; IR (KBr): 1700 cm$^{-1}$; $^1$H-NMR (DMSO-d$_6$): 4.63 (s, 3H, CH$_3$), 8.15 (s, 1H, ArH), 12.1 (broad s, 1H, OH), 13.0 (broad s, 1H, OH).

EXAMPLE 12

7,8-Dihydroxy-3-methyl-3H-1,2,3-triazolo[4,5-f]quinoxaline

A solution of 4,5-diamino-1-methylbenzotriazole (1.2 g, 7.4 mmol) and oxalic acid dihydrate (1.2 g, 9.6 mmol) in 40 ml of 4M hydrochloric acid was refluxed on an oil bath for 2 h and allowed to cool. The resulting precipitate was collected by filtration and washed with water and ethanol to give 1.46 g (91%) of the title compound; m.p. >300° C.; IR (KBr): 1700 cm$^{-1}$; $^1$H-NMR (DMSO-d$_6$): 4.32 (s, 3H, CH$_3$), 7.33 (d, J=9 Hz), 1H, ArH), 7.55 (d, J=9 Hz, 1H, ArH), 12.03 (broad s, 1H, OH), 12.67 (broad s, 1H, OH).

EXAMPLE 13

7,8-Dihydroxy-3-methyl-4-nitro-3H-1,2,3-triazolo[4,5-f]quinoxaline

Finely powdered potassium nitrate (0.47 g, 4.6 mmol) was added portionwise to a stirred solution of 7,8-dihydroxy-3-methyl-3H-1,2,3-triazolo[4,5-f]quinoxaline (1.0 g, 4.6 mmol) in 20 ml of conc. sulfuric acid at 0° C. After 1 h the ice bath was removed and the mixture was stirred over night at room temperature. Then an additional amount of potassium nitrate (0.47 g) was added and stirring was continued over night at room temperature. The solution was poured into ice/water and the precipitated solid was collected, washed with water, and dried to give 1.0 g (83%) of the pure nitro compound; m.p. >300° C.; IR (KBr): 1710 cm$^{-1}$; $^1$H-NMR (DMSO-d$_6$): 4.50 (s, 3H, CH$_3$), 8.18 (s, 1H, ArH), 12.13 (broad s, 1H, OH), 13.17 (broad s, 1H, OH).

EXAMPLE 14

4-Amino-7,8-dihydroxy-3-methyl-3H-1,2,3-triazolo[4,5-f]quinoxaline

A solution of 7,8-dihydroxy-3-methyl-4-nitro-3H-1,2,3-triazolo[4,5-f]quinoxaline (0.78 g, 3 mmol) in ethanol was hydrogenated at atmospheric pressure and room temperature in the presence of 5% palladium-on-charcoal. The catalyst and solid was removed by filtration and washed with ethanol and N,N-dimethylformamide. The combined filtrate was concentrated to dryness giving 30 mg (4%) of the pure amino compound; m.p. >360° C.; IR (KBr): 1680, 1620 cm$^{-1}$. The solid residue containing the catalyst was now treated with hot 2N sodium hydroxide, filtered while hot, and re-precipitated with 4M acetic acid to give the amino compound as a gelatinous product, which was used in the subsequent Sandmeyer reaction without further purification.

EXAMPLE 15

4-Cyano-7,8-dihydroxy-3-methyl-3H-1,2,3-triazolo-4,5-f]quinoxaline

The 4-amino-7,8-dihydroxy-3-methyl-3H-1,2,3-triazolo[4,5-f]quinoxaline isolated above was dissolved in 3 ml of conc. sulfuric acid and cooled on an ice bath. Water (10 ml) was carefully added and the resulting suspension was diazotised with sodium nitrite (0.24 g, 3.4 mmol) in 5 ml of water. After stirring at 0° C. for 30 min, the diazo-suspension was adjusted to pH 7 with saturated aqueous sodium hydrogen carbonate, and a solution of potassium tetracyanonickelate (1.7 g) in 20 ml of water was added in one portion. Stirring was continued for 1 h at 0° C., then the mixture was heated on a steam-bath for 30 min, and cooled. The resulting precipitate was collected by filtration and washed with water. Extraction of the solid with methanol on a Soxhlet apparatus afforded 0.16 g of the cyano compound; m.p. 370° C. dec.; IR (KBr): 2210, 1670 CM$^{-1}$; $^1$H-NMR (DMSO-D$_6$): 4.33 (s, 3H, CH$_3$), 7.57 (s, 1H, ArH), no exchangeable protons could be seen, due to low solubility of the compound; MS (m/z): M$^+$=242.

EXAMPLE 16

7,8-Dihydroxythiazolo[5,4-f]quinoxaline

A solution of 6,7-diaminobenzothiazole (1.3 g, 7.9 mmol) and oxalic acid dihydrate (1.3 g, 10.3 mmol) in 40 ml of 4M hydrochloric acid was refluxed on an oil bath for 1½ h, and cooled. The resulting precipitate was collected by filtration and washed successively with water and ethanol to give 1.52 g (88%) of the title compound; m.p. >360° C.; IR (KBr): 1700 cm$^{-1}$; $^1$H-NMR (DMSO-d$_6$): ca. 6.3 (very broad s, 1H, OH), 7.40 (d, J=9 Hz, 1H, ArH), 7.87 (d, J=9 Hz, 1H, ArH), 9.33 (s, 1H, H-2), 12.07 (broad s, 1H, OH).

EXAMPLE 17

7,8-Dihydroxy-4-nitrothiazolo[5,4-f]quinoxaline

Finely powdered potassium nitrate (92 mg, 0.9 mmol) was added to a stirred and ice-cooled solution of 7,8-dihydroxythiazolo[5,4-f]quinoxaline (0.20 g, 0.9 mmol) in 5 ml of conc. sulfuric acid. The mixture was stirred at 0° C. for 30 min, then at room temperature for 4 h, and finally poured into ice/water. The resulting precipitate was isolated by filtration, washed with water, and dried giving 0.15 g (62%) of the nitro compound; m.p. >360° C., IR (KBr): 1680 cm$^{-1}$; $^1$H-NMR (DMSO-d$_6$): 8.06 (s, 1H, ArH), 9.53 (s, 1H, ArH), 12.23 (broad s, 1H, OH), 12.76 (broad s, 1H, OH).

EXAMPLE 18 a. 5-Amino-2-ethoxycarbonylbenzo[b]thiophene

A suspension of 2-ethoxycarbonyl-5-nitrobenzo[b]-thiophene (5.0 g, 20 mmol) in 500 ml of ethanol was hydrogenated in the presence of 1.8 g of 5% palladium-on-charcoal at room temperature and atmospheric pressure until the required volume of hydrogen (ca. 1.4 l) had been taken up. The catalyst was removed by filtration and washed with ethanol. The filtrate was concentrated to dryness to give 4.2 g (95%) of the amino compound, m.p. 75°–78° C.; $^1$H-NMR (DMSO-d$_6$): 1.32 (t, J=7 Hz, 3H, CH$_3$), 4.30 (q, J=7 Hz, 2H, CH$_2$), 5.22 (broad s, 2H, NH$_2$), 6.87 (dd, J=9, 2 Hz, 1H, H-6), 7.05 (d, J=2 Hz, 1H, H-4), 7.62 (d, J=9 Hz, 1H, H-7), 7.87 (s, 1H, H-3).

b.
5-Ethoxalylamino-2-ethoxycarbonyl-4-nitrobenzo[b]-thiophene

To a stirred solution of 5-amino-2-ethoxycarbonyl-benzo[b]thiophene (1.0 g, 4.5 mmol) and dry triethylamine (0.63 ml, 4.5 mmol) in 7 ml of dry tetrahydrofuran was added dropwise a solution of ethyl oxalylchloride (0.50 ml, 4.5 mmol) in 5 ml of dry tetrahydrofuran under ice-cooling. The reaction mixture was stirred for 1 h at 0° C., and filtered. The filtrate was concentrated to dryness giving 1.46 g (quantitative) of the ethoxalylamino compound. The crude product was nitrated without further purification by adding 0.96 g (3 mmol) portionwise to 10 ml of ice-cooled 80% nitric acid and stirring the mixture at 0° C. for 30 min. Then the mixture was poured into ice-water and the resulting yellow precipitate was isolated by filtration and washed with water to give 0.94 g (86%) of the title compound, m.p. 140°–145° C.; $^1$H-NMR (DMSO-d$_6$): 1.35 (t, J=7 Hz, 6H, 2CH$_3$), 4.35 (q, J=7 Hz, 2H, CH$_2$), 4.37 (q, J=7 Hz, 2H, CH$_2$), 7.92 (d, J=9 Hz, 1H, ArH), 8.17 (s, 1H, H-3), 8.43 (d, J=9 Hz, 1H, ArH), 11.42 (broad s, 1H, NH).

c.
8-Ethoxycarbonyl-2,3-dihydroxythieno[3,2-f]quinoxaline

A solution of 5-ethoxalylamino-2-ethoxycarbonyl-4-nitrobenzo[b]thiophene (0.84 g, 2.3 mmol) in ethanol was hydrogenated at atmospheric pressure and room temperature in the presence of 0.55 g of 5% palladium-on-charcoal. The catalyst was removed by filtration and washed with ethanol. The filtrate was heated to reflux for 1½ h, and cooled. The resulting precipitate was collected by filtration and washed with ethanol to give 0.42 g (63%) of the title compound, m.p. 357°–363° C.; IR (KBr): 1680 cm$^{-1}$; $^1$H-NMR (DMSO-d$_6$): 1.36 (t, J=7 Hz, 3H, CH$_3$), 4.37 (q, J=7 Hz, 2H, CH$_2$), 7.33 (d, J=9 Hz, 1H, ArH), 7.73 (d, J=9 Hz, 1H, ArH), 8.83 (s, 1H, H-9), 12.06 and 12.30 (2 broad s, 2H, 2 OH).

EXAMPLE 19

8-Carboxy-2,3-dihydroxythieno[3,2-f]quinoxaline

8-Ethoxycarbonyl-2,3-dihydroxythieno[3,2-f]quinoxaline (2.0 g, 6.9 mmol) was stirred in 30 ml of 2N sodium hydroxide at room temperature for 2 h. The solution was filtered, and after acidification of the filtrate with 4M hydrochloric acid, the resulting precipitate was collected by filtration and washed with water. The crude product was dissolved in 2N sodium hydroxide and reprecipitated with 4M hydrochloric acid to give 0.94 g (52%) of the carboxylic acid, m.p. >350° C. dec.; IR (KBr): 3300–2200, 1690 cm$^{-1}$.

EXAMPLE 20

4-Chloro-7,8-dihydroxy-1,2,5-selenodiazolo[3,4-f]quinoxaline

A solution of selenium dioxide (0.22 g, 2 mmol) in 20 ml of water was added to a suspension of 5,6-diamino-7-chloro-2,3-dihydroxyquinoxaline (0.45 g, 2 mmol) in 20 ml of ethanol and the mixture was refluxed on an oil bath for 1½ h. After cooling, the deposited solid was collected by filtration and washed with water and ethanol. The crude product was boiled in 200 ml of 2N sodium hydroxide, filtered while hot, and reprecipitated with 4M hydroohloric acid to give 0.46 g (76%) of the Yellow title compound, m.p. >300° C., $^1$H-NMR (DMSO-d$_6$): 7.90 (s, 1H, H-5), 11.93 and 12.10 (2 broad s, 2H, 2 OH).

EXAMPLE 21

(7,8-Dihydroxy-4-sulfamoylthiazolo[5,4-f]quinoxaline 7,8-Dihydroxythiazolo[5,4-f]quinoxaline (0.44 g, 2 mmol) was added portionwise to 2 ml of chlorosulfonic acid with stirring at room temperature. Then the mixture was stirred at 150° C. for 5 h, and left over night at room temperature. The solution was added dropwise to 50 g of crushed ice with stirring. The resulting solid was collected by filtration after 1 h and washed with ice-water and a small amount of ethanol and ether, affording 0.30 g (47%) of crude 4-chlorosulfonyl-7,8-dihydroxythiazolo[5,4-f]quinoxaline. The crude product was stirred with 25 ml of aqueous ammonium hydroxide (25%) for 20 min at room temperature and at 100° C. for 10 min. Nitrogen was bubbled through the hot solution for 5–10 min and after cooling to 0° C. the solution was acidified to pH 1 with 4M hydrochloric acid. The resulting prcipitate was isolated by filtration and dissolved in 150 ml of hot N,N-dimethylformamide. A solid impurity was removed from the hot solution by filtration, and after treatment with charcoal the solution was cooled and evaporated to dryness. The residue was taken up with 15 ml of hot 2N sodium hydroxide, the resulting solution was treated with charcoal, cooled to 0° C. and acidified with 4M hydrochloric acid. The precipitated solid was isolated by centrifugation and washed with water and ethanol to give 60 mg (21%) of the title compound, m.p. >400° C.; IR (KBr): 1710, 1690 cm$^{-1}$; $^1$H-NMR (DMSO-d$_6$): 7.28 (broad s, 2H, NH$_2$), 7.90 (s, 1H, ArH), 9.53 (s, 1H, ArH), 12.17 (broad s, 1H, OH), 12.60 (broad s, 1H, OH).

EXAMPLE 22 a.
6-Chloro-7-ethoxycarbonylamino-2,3-dihydroxyquinoxaline

A solution of 10 g (47,3 mmol) 6-amino-7-chloro-2,3-dihydroxyquinoxaline in 200 ml 0,5N sodium hydroxide was icecooled, and then 30 ml (0,36 mmol) ethyl chloroformate was added. Stirring was continued at 0° C. for 1 h and at 25° C. for 1 h. To the reaction mixture was added 1N hydrochloric acid to pH 2–3, and the precipitated product was filtered off and washed with water to give 12 g of a crude product. Recrystallization (dimethylsulfoxide-0,5N hydrochloric acid) gave 10 g (75%) 6-chloro-7-ethoxycarbonylamino-2,3-dihydroxyquinoxaline, m.p. >300° C. NMR (DMSO-d$_6$): 11.9 (2H, broad s), 8.9 (1H, broad s), 7.37 (1H,s), 7.17 (1H,s), 4.1 (2H,q), 1.28 (3H,t).

b.
7-Chloro-6-ethoxycarbonylamino-5-nitro-2,3-dihydroxyquinoxaline

To an ice-cooled mixture of 50 ml 100% nitric acid and 100 ml glacial acetic acid was added gradually 10 g 6-chloro-7-ethoxycarbonylamino-2,3-dihydroxyquinoxaline. Stirring was continued at 0° C. for 90 min. The reaction mixture was poured into 500 ml ice-water to give 10 g (86%) 7-chloro-6-ethoxycarbonylamino-5-nitro-2,3-dihydroxyquinoxaline as yellow crystals, m.p. >300° C. NMR (DMSO-$d_6$): 12.2 (1H, broad s), 11.7 (1H, broad m), 9.3 (1H, broad s), 7.33 (1H,S), 4.0 (2H,q), 1.2 (3H,t).

c. 6-Amino-7-chloro-5-nitro-2,3-dihydroxyquinoxaline

A mixture of 5 g (15,4 mmol) 7-chloro-6-ethoxycarbonylamino-5-nitro-2,3-dihydroxyquinoxaline and 10 g potassium hydroxide in 60 ml 2-methoxyethanol was refluxed for 15 min. After cooling to 25° C., the reaction mixture was added 20 ml 2-methoxyethanol and 40 ml ether. The precipitated black product was filtered off and washed with ether. The crude product was dissolved in 100 ml water. Addition of 4N hydrochloric acid to pH 5-6 gave 3,4 g (87%) 6-amino-7-chloro-5-nitro-2,3-dihydroxyquinoxaline as red crystals, m.p. >300° C. NMR (DMSO-$d_6$): 12.3 (2H, broad m), 7.40 (1H,s), 6.8 (2H, broad s).

d. 5,6-Diamino-7-chloro-2,3-dihydroxyquinoxaline

A solution of 3 g (11,9 mmol) 6-amino-7-chloro-5-nitro-2,3-dihydroxyquinoxaline in a mixture of 80 ml dimethylformamide and 7,5 ml triethylamine was hydrogenated at atm. pressure using 5% Pd-C (0,5 g) as a catalyst. The reaction mixture was filtered and evaporated in vacuo. The residue was stirred with 100 ml water, added 4N hydrochloric acid to pH 5-6, and the precipitate was filtered off to give 2,1 g of a crude product. Recrystallization (dimethylformamide-methanol) gave 1,95 g (74%) 5,6-diamino-7-chloro-2,3-dihydroxyquinoxaline, m.p. >300° C. NMR (DMSO-$d_6$): 11.6 (1H, broad s), 11.0 (1H, broad m), 6.47 (1H,s), 5.1 (2H, broad s), 4.6 (2H, broad s).

e. 4-Chloro-7,8-dihydroxy-1H-imidazo(4,5-f)quinoxaline

A mixture of 0,3 g (1,35 mmol) 5,6-diamino-7-chloro-2,3-dihydroxyquinoxaline and 8 ml formic acid was refluxed for 2 h. After cooling to 25° C., the reaction mixture was poured into 30 ml water to give 0,21 g (67%) 4-chloro-7,8-dihydroxy-1H-imidazo(4,5-f)quinoxaline, m.p. >300° C. NMR (DMSO-$d_6$): 7.37 (1H,s), 6.70 (1H,s).

EXAMPLE 23 a. 4,5-Diethoxalylaminobenzofurazan

To a solution of 3,6 g (24,0 mmol) 4,5-diaminobenzofurazan in 200 ml dry tetrahydrofuran was added 6,8 ml (48,8 mmol) dry triethylamine. A solution of 5,4 ml (48,0 mmol) ethoxalylchloride in 50 ml dry tetrahydrofuran was added dropwise, and the reaction mixture was left with stirring at 20° C. for 3 h. The mixture was filtered and evaporated to give an oil. The crude product was stirred with methanol to give 3,4 g (81%) 4,5-diethoxalylaminobenzofurazan, m.p. 175,0° C.

b. 7,8-Dihydroxy-1,2,5-oxadiazolo(3,4-f)quinoxaline

A mixture of 2,5 g (7,1 mmol) 4,5-diethoxalylaminobenzofurazan and 20 ml 1N hydrochloric acid was refluxed for 3 h. After cooling to 0° C., the precipitate was filtered off and washed with water to give 1,4 g (97%) 7,8-dihydroxy-1,2,5-oxadiazolo(3,4-f)quinoxaline, m.p. >300° C. NMR (DMSO-$d_6$): 12,8 (1H, broad s), 12.3 (1H, broad s), 7.70 (1H,d), 7.37 (1H,d).

EXAMPLE 24

7,8-Dihydroxy-4-nitro-1,2,5-oxadiazolo(3,4-f)quinoxaline

A solution of 0,4 g (2 mmol) 7,8-dihydroxy-1,2,5-oxadiazolo(3,4-f)quinoxaline in 20 ml concentrated sulfuric acid (95-97%) was ice-cooled and then added 0,2 g (2 mmol) potassium nitrate. Stirring was continued at 0° C. for 30 min. and then at 25° C. for 3 h. The reaction mixture was poured into 100 ml ice-water. Addition of 10N sodium hydroxide to pH 2-3 gave a precipitate (0,44 g). The crude product was recrystallized (methanol-acetone-water) to give 0,38 g (78%) of 7,8-dihydroxy-4-nitro-1,2,5-oxadiazolo(3,4-f)quinoxaline, m.p. >300° C. NMR (DMSO-$d_6$): 12.4 (2H, broad s), 8.47 (1H,s).

EXAMPLE 25 a. 6-Azido-7-chloro-2,3-dihydroxyquinoxaline

A solution of 2 g (9,6 mmol) 6-amino-7-chloro-2,3-dihydroxyquinoxaline in 40 ml 50% fluoroboric acid was added 100 ml water, filtered and then ice-cooled. A solution of 0,68 g (9,9 mmol) sodium nitrite in 20 ml water was added, and after stirring at 0° C. for 15 min. 0,68 g (1,0 mmol) sodium azide dissolved in 20 ml water was added. Stirring was continued at 25° C. for 2 h. The precipitate was filtered off and washed with water to give 1,8 g (80%) 6-azido-7-chloro-2,3-dihydroxyquinoxaline. IR (KBr): 2100 cm$^{-1}$ (N$_3$). NMR (DMSO-$d_6$): 11.7 (2H, broad s), 7.03 (1H,s), 6.93 (1H,s).

b. 6-Azido-7-chloro-2,3-dihydroxy-5-nitroquinoxaline 15 ml 89% nitric acid was ice-cooled and then gradually added 1 g (4,2 mmol) 6-azido-7-chloro-2,3-dihydroxyquinoxaline. After stirring at 0° C. for 15 min, the reaction mixture was poured into 100 ml ice-water. The crude product was recrystallized (acetone-methanol-water) to give 0,95 g (80%) 6-azido-7-chloro-2,3-dihydroxy-5-nitroquinooxaline. IR (KBr): 2450 cm$^{-1}$ (N$_3$). NMR (DMSO-$d_6$): 12.3 (2H, broad s), 7.07 (1H,s).

c. 4-chloro-7,8-dihydroxy-1,2,5-oxadiazolo(3,4-f)quinoxaline-1-oxide

A mixture of 1 g (3,5 mmol) 6-azido-7-chloro-2,3-dihydroxy-5-nitroquinoxaline and 15 ml xylene was refluxed for 3 h. After cooling to 25° C. the precipitate was filtered off and washed with toluene and ether to give 0,86 g (96%) 4-chloro-7,8-dihydroxy-1,2,5-oxadiazolo(3,4-f)quinoxaline-1-oxide, m.p. >300° C. NMR (DMSO-$d_6$): 12.6 (1H, broad s), 12.0 (1H, broad s), 7.10 (1H,s).

EXAMPLE 26

4-Chloro-7,8-dihydroxy-2-trifluoromethyl-1H-imidazo(4,5-f)quinoxaline

A mixture of 0,3 g (1,35 mmol) 5,6-diamino-7-chloro-2,3-dihydroxyquinoxaline and 8 ml trifluoroacetic acid was refluxed for 3 h. After cooling to 0° C., the precipitated product was filtered off and washed with ice-cooled trifluoroacetic acid and ether to give 0,28 g (68%) 4-chloro-7,8-dihydroxy-2-trifluoromethyl-1H-imidazo(4,5-f)quinoxaline, m.p. >300° C. NMR (DMSO-$d_6$): 7.10 (1H,s).

EXAMPLE 27 a. 4-chloro-7,8-dihydroxy-1,2,5-oxadiazolo(3,4-f)quinoxaline

To a solution of 0,6 g (2,4 mmol) 4-chloro-7,8-dihydroxy-1,2,5-oxadiazolo(3,4-f)quinoxaline-1-oxide in a mixture of 14 ml ethanol and 3 ml dimethylformamide was added 0,9 ml (5,3 mmol) triethyl phosphite. The mixture was refluxed for 4 h, and then evaporated in vacuo. The residue was stirred with water and then with ether-ethyl acetate (5:1) to give 0,4 g (71%) 4-chloro-7,8-dihydroxy-1,2,5-oxadiazolo-(3,4-f)quinoxaline, m.p. >300° C. NMR (DMSO-$d_6$+$D_2O$): 7.40 (1H,s).

EXAMPLE 28

6-Chloro-2,3-dihydroxy-8,9-dimethylpyrazino(2,3-f)quinoxaline

A mixture of 0,5 g (2,24 mmol) 5,6-diamino-7-chloro-2,3-dihydroxyquinoxaline in 10 ml water was at 50° C. added a solution of 0,4 g (4,6 mmol) 2,3-butanedione in 5 ml water. The reaction mixture was stirred at 50° C. for 24 h. After cooling to 25° C., the precipitate was filtered off and washed with water and ethanol to give 0,3 g (50%) 6-chloro-2,3-dihydroxy-8,9-dimethyl-pyrazino(2,3-f)quinoxaline, m.p. >300° C. NMR (DMSO-$d_6$): 8.47 (1H,s), 2.60 (3H,s), 2.53 (3H,s).

EXAMPLE 29

6-Chloro-2,3-dihydroxypyrazino(2,3-f)quinoxaline

A mixture of 0,5 g (2,24 mmol) 5,6-diamino-7-chloro-2,3-dihydroxyquinoxaline in 20 ml water was added 0,5 ml (3,36 mmol) 40% aqueous glyoxal and 0,35 g (3,36 mmol) sodium carbonate. The reaction mixture was stirred at 50° C. for 3 h. After cooling to 25° C., the precipitate was filtered off. The crude product was stirred with water and added 1N hydrochloric acid to pH 2-3 to give 0,56 g (100%) 6-chloro-2,3-dihydroxypyrazino(2,3-f)quinoxaline, m.p. >300° C. NMR (DMSO-$d_6$): 9.0 (2H,s), 7.73 (1H,s).

EXAMPLE 30

4-Chloro-7,8-dihydroxy-2-methyl-1H-imidazo(2,3-f)quinoxaline

A mixture of 0,5 g (2,24 mmol) 5,6-diamino-7-chloro-2,3-dihydroxyquinoxaline and 0,33 g (3,3 mmol) 2,4-pentanedione in 20 ml glacial acetic acid was stirred at 100° C. for 30 min. After cooling to 25° C., the precipitate was filtered off and washed with glacial acetic acid and ether to give 0,53 g (100%) 4-chloro-7,8-dihydroxy-2-methyl-1H-imidazo(2,3-f)quinoxaline, m.p. >300° C. NMR (DMSO-$d_6$): 7.0 (1H,s), 2.53 (3H,s).

EXAMPLE 31

2,3-Dihydroxy-8,10-dimethyl-7H-pyrazino(2,3-g)(1,5)benzodiazepine

A mixture of 0,5 g (2,24 mmol) 5,6-diamino-7-chloro-2,3-dihydroxyquinoxaline and 1,0 g (10 mmol) 2,4-pentanedione in 15 ml glacial acetic acid was stirred at 25° C. for 20 h. The precipitate was filtered off and washed with ethanol and ether to give 0,43 g (67%) 2,3-dihydroxy-8,10-dimethyl-7H-pyrazino(2,3-g)(1,5)benzodiazepine, m.p. >300° C. NMR (DMSO-$D_6$): 7.07 (2H,s), 2.33 (3H,s), 2.27(3H,s).

EXAMPLE 32 a. 5,6-Diamino-2,3-dihydroxyquinoxaline

A solution of 5,0 g (24,5 mmol) 7,8-dihydroxy-1,2,5-oxadiazolo(3,4-f)quinoxaline and 6,8 ml (49 mmol) triethylamine in 500 ml dimethylformamide was hydrogenated at atm. pressure using 5% Pd-C (0,5 g) as a catalyst. The reaction mixture was filtered and evaporated in vacuo. The residue was stirred with water, and the precipitate was filtered off to give 4,5 g (96%) 5,6-diamino-2,3-dihydroxyquinoxaline, m.p. >300° C. NMR (DMSO-$d_6$): 11.0 (2H, broad m), 6.43 (1H,d), 6.23 (1H,d), 4.5 (4H, broad m).

b. 2,3-Dihydroxy-8,9-dimethylpyrazino(2,3-f)quinoxaline

A mixture of 0,5 g (2,6 mmol) 5,6-diamino-2,3-dihydroxyquinoxaline and 10 ml water was at 50° C. added a solution of 0,45 g (5,2 mmol) 2,3-butanedione in 5 ml water. The reaction mixture was stirred at 50° C. for 4 h. After cooling to 25° C., the precipitate was filtered off and washed with water. The crude product was dissolved in 2N sodium hydroxide and reprecipitated with 2N hydrochloric acid to pH 6-7 to give 0,4 g (64%) 2,3-dihydroxy-8,9-dimethylpyrazino(2,3-f)quinoxaline, m.p. >300° C. NMR (DMSO-$d_6$): 7.27 (1H,d), 6.93 (1H,d), 2.07 (6H,s).

EXAMPLE 33

7,8-Dihydroxy-2-methyl-1H-imidazo(2,3-f)quinoxaline

A mixture of 0,5 g (2,56 mmol) 5,6-diamino-2,3-dihydroxyquinoxaline and 0,52 g (5,2 mmol) 2,4-pentanedione in 20 ml glacial acetic acid was stirred at 100° C. for 1,5 h. After cooling to 25° C., the precipitate was filtered off and washed with water and ethanol to give 0,56 g (100%) 7,8-dihydroxy-2-methyl-1H-imidazo(2,3-f)quinoxaline, m.p. >300° C. NMR (DMSO-$d_6$): 7,17 (1H,d), 6.93 (1H,d), 2.53 (3H,s).

EXAMPLE 34

2,3-Dihydroxypyrazino(2,3-f)quinoxaline

A mixture of 0,5 g (2,6 mmol) 5,6-diamino-2,3-dihydroxyquinoxaline and 20 ml water was added 0,6 ml (3,9 mmol) 40% aqueous glyoxal and 0,41 g (3,9 mmol) sodium carbonate. The reaction mixture was stirred at 50° C. for 1,5 h. After cooling to 25° C., the precipitate was filtered off and washed with water. to give 0,49 g. The crude product was dissolved in 2N sodium hydroxide and reprecipitated with 2N hydrochloric acid to pH 6-7 to give 0,2 g (36%) 2,3-dihydroxypyrazino(2,3-f)quinoxaline, m.p. >300° C. NMR (DMSO-$d_6$): 8.30 (1H,d), 8.20 (1H,d), 7.27 (1H,d), 7.0 (1H,d).

EXAMPLE 35

2,3-Dihydroxy-6-nitropyrazino(2,3-f)quinoxaline

To a solution of 0,38 g (1,4 mmol) 2,3-dihydroxypyrazino(2,3-f)quinoxaline in 25 ml concentrated sulfuric acid was added at 0° C. 0,28 g (2,8 mmol) potassium nitrate. Stirring was continued at 0° C. for 30 min. and at 25° C. for 24 h. The reaction mixture was poured into 100 ml ice-water. The solution was added 10N sodium hydroxide to pH 7, and then extracted with ethyl acetate (5×100 ml). The combined and dried ethyl acetate phases were evaporated to give 0,17 g (47%) 2,3-dihydroxy-6-nitropyrazino(2,3-f)quinoxaline, m.p. >300° C. NMR (DMSO-$d_6$): 9.10 (2H,s), 8.23 (1H,s).

EXAMPLE 36

2,3-Dihydroxy-8,9-dimethyl-6-nitropyrazino(2,3-f)quinoxaline

To a solution of 0,45 g (1,9 mmol) 2,3-dihydroxy-8,9-dimethylpyrazino(2,3-f)quinoxaline in 30 ml concentrated sulfuric acid was added at 0° C. 384 mg (3,8 mmol) potassium nitrate. Stirring was continued at 0° C. for 30 min. and at 25° C. for 24 h. The reaction mixture was poured into 150 ml icewater. The solution was added 10N sodium hydroxide to pH 7, and then extracted with ethyl acetate (5×100 ml). The combined and dried ethyl acetate phases were evaporated to give 0,18 g (33%) 2,3-dihydroxy-8,9-dimethyl-6-nitropyrazino(2,3-f)quinoxaline, m.p. >300° C. NMR (DMSO-$d_6$): 8.07 (1H,s), 2.77 (3H,s), 2.73 (3H,s).

EXAMPLE 37 a. 4,5-Diethoxalylamino-1,2,5-benzothiadiazole

To a mixture of 2,0 g (12,0 mmol) 4,5-diamino-1,2,5-benzothiadiazole and 5,0 ml (32 mmol) dry triethylamine in 100 ml dry tetrahydrofuran was added dropwise a solution of 3,0 ml (27 mmol) ethoxalylchloride in 35 ml dry tetrahydrofuran. Stirring was continued at 25° C. for 2 h. The reaction mixture was filtered and evaporated in vacuo. The residue was stirred with water, and the mixture was extracted with ethyl acetate (2×50 ml). The combined and dried ethyl acetate phases were evaporated to give 3,0 g (68%) 4,5-diethoxalylamino-1,2,5-benzothiadiazole, m.p. 168,5° C. NMR (DMSO-$d_6$): 10.8 (1H, broad s), 10.6 (1H, broad s), 8.03 (2H,s), 4.3 (4H,q), 1.33 (6H,t).

b. 7,8-Dihydroxy-1,2,5-thiadiazolo(3,4-f)quinoxaline

A mixture of 1,0 g (2,73 mmol) 4,5-diethoxalylamino-1,2,5-benzothiadiazole and 5 ml ethanol and 10 ml 1N hydrochloric acid was refluxed for 2 h. The reaction mixture was added 10 ml water, cooled to 25° C., and filtered to give 0,57 g (95%) 7,8-dihydroxy-1,2,5-thiadiazolo(3,4-f)quinoxaline, m.p. >300° C. NMR (DMSO-$d_6$): 12.5 (1H, broad s), 12.2 (1H, broad s), 7.73 (1H,d), 7.47 (1H,d).

EXAMPLE 38

7,8-Dihydroxy-4-nitro-1,2,5-thiadiazolo(3,4-f)quinoxaline

To a solution of 0,4 g (1,8 mmol) 7,8-dihydroxy-1,2,5-thiadiazolo(3,4-f)quinoxaline in 20 ml concentrated sulfuric acid was added at 0° C. 0,19 g (1,9 mmol) potassium nitrate. Stirring was continued at 0° C. for 30 min. and at 25° C. for 24 h. The reaction mixture was poured into 100 ml ice-water to give 0,34 g (71%) 7,8-dihydroxy-4-nitro-1,2,5-thiadiazolo(3,4-f)quinoxaline as a precipitate, m.p. >300° C. NMR (DMSO-$d_6$): 12,3 (1H, broad s), 11.6 (1H, broad s), 8.43 (1H,s).

EXAMPLE 39

2,3-Dihydroxythieno[3,2-f]quinoxaline

A solution of 5-amino-4-nitrobenzo[b]thiophene (0.50 g, 2.6 mmol) in 50 ml of 96% ethanol was hydrogenated at room temperature and atm. pressure in the presence of 5% palladium-on-carbon until the theoretical amount of hydrogen was absorbed. The catalyst was filtered off, and the filtrate was acidified with 1N hydrochloric acid and evaporated to dryness. The residue was refluxed with oxalic acid dihydrate (0.40 g, 3.1 mmol) in 25 ml of 4M hydrochloric acid for 2 h. The mixture was cooled, and the precipitated solid was isolated by filtration, washed with water, ethanol and ether, and dried. The crude product was dissolved in a minimum amount of 2N sodium hydroxide, treated with decolourising charcoal, and filtered. The filtrate was acidified with 4M hydrochloric acid and the resulting precipitate was collected by filtration, washed with water, ethanol and ether to give 0.22 g (39%) of the thienoquinoxaline; m.p. 186.6° C.; IR (KBr): 1680 cm$^{-1}$; H-NMR (DMSO-$d_6$): 7.13 (d,J=9 Hz, 1H, ArH), 7.62 (D,J=9 Hz, 1H, ArH), 7.72 (d,J=5 Hz, 1H, ArH), 7.95 (d,J=5 Hz, 1H, ArH); MS m/z: 218 (M+, 100%).

The pharmaceutical preparations or compositions comprising the compounds of the invention may be administered to humans or animals by oral or parenteral route.

An effective amount of the active compound or a pharmaceutically-acceptable salt thereof may be determined in accordance with the usual factors, such as the nature and severity of the condition and the weight of the mammal requiring treatment.

Conventional excipients are such pharmaceutically-acceptable organic or inorganic carrier substances suitable for parenteral or enteral application which do not deleteriously react with the active compounds.

Examples of such carriers are water, salt solutions, alcohols, polyethylene glycols, polyhydroxyethoxylated castor oil, gelatine, lactose, amylose, magnesium stearate, talc, silicic acid, fatty acid monoglycerides and diglycerides, pentaerythritol fatty acid esters, hydroxymethylcellulose, and polyvinylpyrrolidone.

The pharmaceutical preparations can be sterilized and mixed, if desired, with auxiliary agents, such as lubricants, preservatives, stabilizers, wetting agents, emulsifiers, salt for influencing osmotic pressure, buffers and/or coloring substances and the like, which do not deleteriously react with the active compounds.

Injectable solutions or suspensions, preferably aqueous solutions with the active compound dissolved in polyhydroxylated castor oil, are particularly suitable for parenteral administration.

Ampoules are conveniently unit dosages.

Tablets, dragees, or capsules containing talc and/or a carrier or binder or the like are particularly suitable for oral administration. The carrier preferably is lactose and/or corn starch and/or potato starch.

A syrup, elixir, or the like can be used in the cases where a sweetened vehicle can be employed or is desired.

Generally, the compounds of this invention are dispensed in unit dosage form comprising 10-200 mg of active ingredient in or together with a pharmaceutically-acceptable carrier per unit dosage.

The dosage of the compounds according to this invention is 1-500 mg/day, when administered to patients, e.g., humans, as a drug.

A typical tablet which may be prepared by conventional tabletting techniques contains:

| Core: | |
|---|---|
| Active compound (as free compound or salt thereof) | 100 mg |
| Colloidal silicon dioxide (Aerosil ®) | 1.5 mg |
| Cellulose, microcryst. (Avicel ®) | 70 mg |
| Modified cellulose gum (Ac-Di-Sol ®) | 7.5 mg |
| Magnesium stearate | 1 mg |
| Coating: | |

| | |
|---|---|
| HPMC | approx. 9 mg |
| *Mywacett 9-40 T ® | approx. 0.9 mg |

*Acylated monoglyceride used as plasticizer for film-coating

The free compounds of the present invention which form alkali metal or alkaline earth metal salts may be employed in such salt form. Such alkali metal or earth alkali metal salts are ordinarily formed by reacting the dihydroxyquinoxaline compound with an equivalent amount or excess of the selected alkali metal or earth alkali metal as the hydroxide frequently and suitably by admixture in the presence of a neutral solvent, from which the salt may be precipitated or recovered in other conventional manner, e.g., by evaporation. Administration of a compound of the invention is often preferably in the form of a pharmaceutically-acceptable watersoluble alkali metal or earth alkali metal salt thereof, and orally, rectally, or parenterally in the form of a pharmaceutical composition wherein it is present together with a pharmaceutically-acceptable liquid or solid carrier or diluent.

The compounds of the invention, together with a conventional adjuvant, carrier, or diluent, may be placed into the form of pharmaceutical compositions and unit dosages thereof, and in such form may be employed as solids, such as tablets or filled capsules, or liquids, such as solutions, suspensions emulsions. elixirs, or capsules filled with the same. all for oral use, in the form of suppositories for rectal administration; or in the form of sterile injectable solutions for parenteral (including subcutaneous) use. Such pharmaceutical composition and unit dosage forms thereof may comprise conventional ingredients in conventional proportions, with or without additional active compounds or principles, and such unit dosage forms may contain any suitable effective glutamate antagonistic, amount of the active ingredient commensurate with the intended daily dosage range to be employed. Tablets containing fifty (50) milligrams of active ingredient or, more broadly, ten (10) to two hundred (200) milligrams, per tablet, are accordingly suitable representative unit dosage forms.

Due to their high degree of glutamate antagonistic activity and their low toxicity, together presenting a most favorable therapeutic index, the compounds of the invention may be administered to a subject, e.g., a living animal body, in need of such glutamate antagonist treatment. elimination. alleviation, or amelioration of an indication which is sensitive to a change in the glutamate receptor condition, e.g., epilepsy, psychosis, dementia, convulsion, or muscle rigidity, often preferably in the form of an alkali metal or earth alkali metal salt thereof, concurrently, simultaneously, or together with a pharmaceutically-acceptable carrier or diluent. especially and preferably in the form of a pharmaceutical composition thereof, whether by oral, rectal, or parenteral (including subcutaneous) route, in an effective amount. Suitable dosage ranges are 1–500 milligrams daily, preferably 10–200 milligrams daily, and especially 50–100 milligrams daily, depending as usual upon the exact mode of administration, form in which administered, the indication toward which the administration is directed, the subject involved and the body weight of the subject involved, and the preference and experience of the physician or veterinarian in charge. Such method of treating may be described as the treatment of an indication caused by or related to hyperactivity of the excitatory neurotransmitters, in a subject in need thereof, which comprises the step of administering to the said subject a neurologically-effective amount of a glutamate antagonistic heterocyclic compound of the invention.

In conclusion, from the foregoing, it is apparent that the present invention provides novel neurologically-effective glutamate antagonistic heterocyclic compounds and salts thereof, having advantageous and unpredictable properties, as well as novel pharmaceutical compositions thereof and method of treating therewith, all possessed of the foregoing more specifically-enumerated characteristics and advantages.

It is to be understood that the invention is not to be limited to the exact details of operation, or to the exact compositions, methods, procedures, or embodiments shown and described, as obvious modifications and equivalents will be apparent to one skilled in the art, and the invention is therefore to be limited only by the full scope of the appended claims.

We claim:

1. A heterocyclic compound selected from those having the formula I

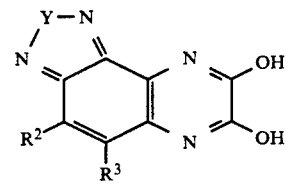

wherein
$R^2$ is hydrogen, $NO_2$, $NH_2$, $CN$, halogen, or $SO_2NH_2$;
—X—Y—Z— is selected from $=N-Se-N=$, $=N-O-N=$ and $=N-S-N=$;
wherein $R^3$ is hydrogen, lower alkyl, or $CF_3$ and a pharmaceutically-acceptable salt thereof.

2. A compound according to claim 1 which is 4-chloro-7,8-dihydroxy-1,2,5-oxadiazolo(3,4-f)quinoxaline.

3. A compound according to claim 1 which is 4-chloro-7,8-dihydroxy-1,2,5-selenodizaolo[3,4-f]quinoxaline.

4. A compound according to claim 1 which is 7,8-dihydroxy-1,2,5-thiadiazolo(3,4-f)quinoxaline.

5. A compound according to claim 1 which is 7,8-dihydroxy-4-nitro-1,2,5-thiadiazolo(3,4-f)quinoxaline.

6. A pharmaceutical composition comprising as active glutamate antogonistic component a heterocyclic compound according to claim 1 and a pharmaceutically acceptable carrier.

7. A pharmaceutical composition according to claim 6 in the form of an oral dosage unit containing about 10–200 mg of the active compound.

8. A method of treating hyperactivity of the excitatory neurotransmitters, in a subject in need thereof, which comprises the step of administering to the said subject a neurologically-effective, glutamate antagonistic, amount of a heterocyclic compound of claim 1.

9. A compound according to claim 1 which is 7,8-Dihydroxy-1,2,5-oxadiazolo(3,4-f)quinoxaline.

10. A compound according to claim 1 which is 7,8-Dihydroxy-4-nitro-1,2,5-oxadiazolo(3,4-f)quinoxaline.

11. 4-Chloro-7,8-dihydroxy-1,2,5-oxadiazolo(3,4-f)quinoxaline-1-oxide.

* * * * *

UNITED STATES PATENT AND TRADEMARK OFFICE
CERTIFICATE OF CORRECTION

PATENT NO. : 5,109,001               Page 1 of 2
DATED       : April 28, 1992
INVENTOR(S) : Poul Jacobsen, Flemming E. Nielsen, Tage Honoré, Jorgen Drejer It is certified that error appears in the above-indentified patent and that said Letters Patent is hereby corrected as shown below:

Title Page, Column 2 [57] ABSTRACT, four lines below the formula, "-NV$^{3/}$," should read -- -N=,$_3$--.
Column 1, line 27; move the "$^3$" from the beginning of line 26 and insert at the end of line 25 after "NR"$_3$ and before the hyphen.
Column 4, line 40; "H-AMPA" should read --$^3$H-AMPA--.
Col. 4, line 59, "(2 pg/ml) should read --(2 µg/ml)--
Column 5, line 16; "Nacl," should read -- NaCl, --.
Column 5, line 17; "Cacl$_2$" should read -- CaCl$_2$ --.
Column 12, line 62; move the "y" at the beginning of line 62 to the end of line 61 and insert before the hyphen.
Column 15, approximately line 33; "-2.3-dihydroxypyrazino" should read -- -2,3-dihydroxypyrazino --.
Column 15, approximately line 33 (second occurrence) "(2.3-f)" should read -- (2,3-f) --.
Column 15, line 42; "(2.3-f)" should read -- (2,3-f) --.
Column 16, line 20; "2.3-butanedione" should read -- 2,3-butanedione --.
Column 19, line 12; "hydroxide frequently" should read -- hydroxide, frequently --.

UNITED STATES PATENT AND TRADEMARK OFFICE
CERTIFICATE OF CORRECTION

PATENT NO. : 5,109,001

DATED : Apr. 28, 1992

INVENTOR(S) : Poul Jacobsen, Flemming E. Nielsen, Tage Honoré, Jorgen Drejer

It is certified that error appears in the above-identified patent and that said Letters Patent is hereby corrected as shown below:

```
Column 19, approximately line 28; "emulsions. elixirs,"
   should read -- emulsions, elixirs, --.
Column 19, approximately line 29; "same.all"
   should read -- same, all --.
Column 19, approximately line 49; "ment. elimination."
   should read -- ment, elimination, --.
```

Signed and Sealed this

Twenty-sixth Day of October, 1993

*Attest:*

BRUCE LEHMAN

*Attesting Officer*  *Commissioner of Patents and Trademarks*